United States Patent [19]

Borchard et al.

[11] Patent Number: 4,621,085
[45] Date of Patent: Nov. 4, 1986

[54] 2,4,7-TRIAMINO-6-PHENYLPTERIDINE

[75] Inventors: Ulrich Borchard, Grevenbroich; Ernst Mutschler, Mainz-Hechtsheim; Werner Moehrke, Seeheim-Jugenheim; Karl-Dieter Voelger, Bickenbach; Erwin Wolf, Darmstadt, all of Fed. Rep. of Germany

[73] Assignee: Rohm GmbH Chemische Fabrik, Darmstadt, Fed. Rep. of Germany

[21] Appl. No.: 719,570

[22] Filed: Apr. 3, 1985

[30] Foreign Application Priority Data

Apr. 5, 1984 [DE] Fed. Rep. of Germany ....... 3412765

[51] Int. Cl.$^4$ .................... A61K 31/50; A61K 31/495
[52] U.S. Cl. ..................................... 514/249; 514/821
[58] Field of Search ............................... 514/249, 821

[56] References Cited

U.S. PATENT DOCUMENTS

| 3,081,230 | 3/1963 | Smith et al. | 514/222 |
| 4,118,492 | 10/1978 | Voelger et al. | 424/251 |
| 4,252,809 | 2/1981 | Knauf et al. | 514/249 |
| 4,425,345 | 1/1984 | Horlington et al. | 514/249 |
| 4,425,346 | 1/1984 | Horlington et al. | 514/249 |

FOREIGN PATENT DOCUMENTS

| 51-6193 | 1/1976 | Japan. | |
| 51-81877 | 7/1976 | Japan. | |
| 932256 | 7/1963 | United Kingdom | 514/249 |
| 998284 | 7/1965 | United Kingdom. | |
| 1313937 | 4/1973 | United Kingdom. | |
| 2018133 | 10/1979 | United Kingdom. | |

OTHER PUBLICATIONS

Chem. Abst. 95: 181,123(x) (1981)–Poole-Wilson.
Chem. Abst. 89: 117,889(a) (1978)–Fleckenstein et al.
Chem. Abst. 88: 146,338e (1978)–Erdmann et al.
Chem. Abst. 87: 47976j (1977)–Naumann et al.
Chem. Abst. 83: 126334u (1975)–Seller et al.
Chem. Abst. 83: 90801c (1975)–Seller et al.
Chem. Abst. 83: 520h (1975)–Yeh et al.
J. Med. Chem. vol. 11 (1968) pp. 573–579, "Structure Activity Relationships of some Pteridine Diuretics", Joseph Weinstock et al, 1/6/68.

Medicinal Chemistry, "52 Topics in Current Chemistry", Ariens et al, pp. 43–51.
Reprint from Archives Internationales de Pharmacodynamie et de Therapie, vol. 256, No. 2, pp. 253–268, "Characterization of Antiarrhythmic Drugs by Alternating Current Induced Arrhythmias in Isolated Heart Tissues", Borchard et al, Apr. 1982.
Arzneimittel-Forschung Drug Research, "The Positive Inotropic Action of Triamterene in Isolated Heart Tissues, Borchard et al, pp. 3–19, 1980.
American Heart Journal, vol. 89, No. 4, pp. 493–500, Seller et al, "Cardiac Effect of Diuretic Drugs", Apr. 1975.
Calciumantagonisten zur Behandlung der Angina pectoris, Hypertonie und Arrhythmie, 1982 Excerpta Medica, pp. 3–6, Bender and Greeff.
Arzneim-Forsch (Drug Res.) 26, 10, 1812–1817, 1976, reprint pp. 1–3, Erdmann and Krawietz.
Archives Internationales de Pharmacodynamie et de Thérapie, 256, No. 2, Apr. (1982) U. Borchard et al, Characterization of Antiarrhythmic Drugs by Alternating Current Induced Arrhythmias. . . ".
Arzneim. Forsch./Drug Res. 31 (1981) U. Borchard et al, "The Positive Inotropic Action of Triamterene on Isolated Heart Tissues".

Primary Examiner—Douglas W. Robinson
Attorney, Agent, or Firm—Oblon, Fisher, Spivak, McClelland, & Maier

[57] ABSTRACT

The present invention relates to pharmaceutical preparations with cardiac, particularly anti-arrhythmic activity. These preparations comprise, as an active principle, at least one compound of formula I:

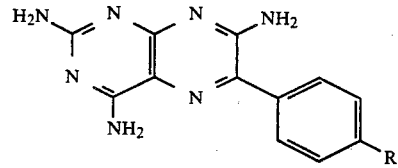

where R represents a lipophilic radical.

The pharmaceutical compositions may comprise this compound in the presence of other pharmaceutical excipients and adjuvants.

6 Claims, No Drawings

2,4,7-TRIAMINO-6-PHENYLPTERIDINE

BACKGROUND OF THE INVENTION

1. Field of the Invention

The invention relates to pharmaceutical preparations with cardiac, particularly antiarrhythmic, activity.

2. Description of the Prior Art

Some diuretic and anti-hypertensive triaminoarylpteridine compounds are disclosed in U.S. Pat. No. 3,081,230. Among these, 2,4,7-Triamino-6-phenylpteridine and certain of its derivatives have shown the greatest activity in this area. Thus 2,4,7-triamino-6-phenylpteridine, under the name triamterene, has acquired major therapeutic importance due to its anti-kaliuretic action.

The general disclosure in U.S. Pat. No. 3,081,230 provides substituents on the para-position of the phenyl ring situated on the 6-position of the pteridine molecule. These substituents include alkyl and alkoxy groups containing up to 3 carbon atoms, a trifluoromethyl group or a halogen atom.

More specifically, the p-chloro-, p-trifluoromethyl- and p-fluorophenyl compounds are described in this U.S. patent.

U.S. Pat. No. 3,081,230, however, contains no further data on the pharmaceutical applicability of these compounds.

The present inventors have conducted a broadly based scientific study which yielded over a hundred structure activity relations for pteridine derivatives (J. Weinstock et al., *J. Med. Chem.* (1968) 11:573–579; "Therapie mit Triamteren", 1966, in: Wiener Symposium, chaired by K. Fellinger, pub. Georg Thieme Verlag, Stuttgart, 1968.)

The present inventors summarized their results regarding the effects of substitutions on the phenyl group as follows: "In Table VIII is shown the diuretic activity of compounds in which the phenyl of triamterene has been replaced by a substituted phenyl. Here again, only small changes are permissible if even modest diuretic activity is to be retained". (Weinstock et al., loc. cit., p. 578.)

In fact, the data appears to support the hypothesis that neither hydrophilic substitution, e.g. —OH, —NH or

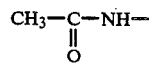

nor lipophilic substitution, e.g. $CH_3$—, F— or $C_6H_5$— in the para position of the phenyl group leads to pharmaceutically valuable compounds.

Further study has shown that hydrophilic substitution does not eliminate diuretic and anti-kaliuretic activity for triamterene derivatives.

Thus, it has been surprising discovered that, in equimolar concentrations, the triamterene metabolites p-hydroxytriamterene (phase I metabolite) and hydroxytriamterene sulfuric acid ester (phase II metabolite) have practically the same activity for electrolyte transport as triamterene itself. (H. Knauf et al., Arzneim.-Forsch./Drug Res. (1978) 28, (II):1417–1420; U.S. Pat. No. 4,118,492.)

High diuretic, anti-kaliuretic, anti-hypertensive, and cardioprotective activity is known for derivatives of p-hydroxytriamterene with pronounced hydrophilic substitution (See British Pat. No. 2,018,133).

According to the prior art, however, non-hydrophilic substituted derivatives of triamterene do not appear to have any recognizable therapeutic potential. Moreover, there was the generally recognized latent hazard that these pteridine derivatives would have folic acid antagonist properties, which are not possessed by triamterene itself to any appreciable degree (see Fellinger, loc. cit.).

Triamterene and its therapeutically recommended derivatives are a well studied class of substances with relatively insignificant side effects. These compounds are also easy to study analytically.

It is well known that cardiac disorders are responsible for a large percentage of the causes of death in industrial countries. In particular, cardiac arrhythmias play a significant role in these fatal disorders. Pathological changes in heartbeat frequency are generally attributable to disturbances in the formation or conduction of the excitation phase of the heart beat. Depending on the type of disturbances present (e.g., bradycardia, tachycardia, or arrythmia) the medication employed (anti-arrhythmic or anti-fibrillatory) will be such as to accelerate the heartbeat, to decelerate the heartbeat, or to eliminate irregularities.

Examples of frequently used anti-fibrillatory substances are:
 (i) quinidine (a diastereomer of quinine);
 (ii) the rauwolfia alkaloid ajmaline;
 (iii) the coronary therapeutic agent verapamil;
 (iv) the local anesthetics procainamide and lidocaine;
 (v) the anti-epileptic phenytoin; and
 (vi) beta-blocking agents.

As is seen, these are substances with markedly different chemical structures.

In general anti-fibrillatory activity is connected with a reduction of excitation formation and excitation conduction in the cells of a specific excitation conduction system and of the working myocardium. The anti-fibrillatories, as a rule, act negatively inotropically. Therefore, in general they are contraindicated in cases of cardiac insufficiency. Moreover, the alkaloids and other substances mentioned above are often not well tolerated and/or generate allergic reactions with patients undergoing treatment.

Accordingly, there is a persistent need for a new anti-arrhythmic substance.

SUMMARY OF THE INVENTION

Accordingly, it is an object of the present invention to provide a novel pharmaceutical composition having cardiac activity.

It is another object of the present invention to provide a novel pharmaceutical composition having anti-arrhythmic activity.

It is another object of this invention to provide a novel method for treating cardiac disorders.

It is another object of this invention to provide a novel method for treating cardiac arrhythmias.

These and other objects have been surprisingly satisfied by the discovery that compounds having formula I:

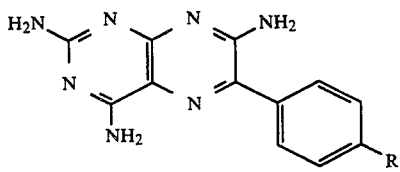

wherein R is a lipophilic radical, are cardiac-active, and, particularly, anti-arrhythmically active.

DESCRIPTION OF THE PREFERRED EMBODIMENTS

The compounds of the present invention are characterized by having formula I:

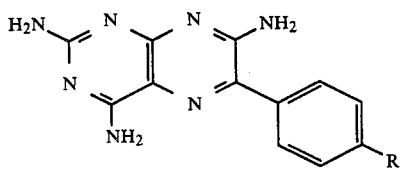

wherein R is a lipophilic radical.

Preferably R in the formula is:

(1) a halogen, such as F, Cl, Br, or iodine; F and Cl are preferred;
(2) an alkyl group having 1 to 6 carbon atoms, and which may be a linear, a branched or a cyclic alkyl group which is either saturated or unsaturated; branched and cyclic alkyl groups are preferred;
(3) a benzyl group;
(4) a trifluoromethyl group; or
(5) a nitro group.

These compounds are cardiac-active. In particular they are anti-arrhythmic active.

Some of the compounds of formula I are known.

These compounds can be prepared by reacting para-substituted phenylacetonitriles of formula II

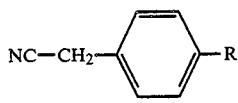

where R has the same meaning as above, with 2,4,6-triamino-5-nitrosopyrimidine under basic catalysis conditions. The prepartions are run analogously to the method of R. G. W. Spickett and G. M. Timmis (*J. Chem. Soc.* (1954) 2887).

The compounds having formula I are as a rule yellow, crystalline, high melting compounds which fluoresce strongly under uv light.

Particularly preferred compounds are compounds where R is a fluorine or a chlorine atom, or one of the following groups: trifluoromethyl, isopropyl, sec-butyl, tert-butyl, neopentyl, cyclohexyl, or benzyl.

Characterization of a substance as an antiarrhythmic may be accomplished as follows. For example, a testing protocol may be used where arrhythmias asystoles are induced in guinea pigs by means of a 50 Hz alternating current voltage applied to the isolated left atrium of the heart and to the right ventricular papillary muscle (see V. Borchard, R. Boesken, and K. Greeff, 1982, *Arch. Intern. Pharmacodyn. Therap.* 256, 2:253).

Properties and activities of the lipophilic triamterene derivatives of formula I will be described hereinbelow using the example of 2,4,7-triamino-6-(4'-fluorophenyl)-pteridine ("p-fluorotriamterene"). This compound meets the requirements for an anti-arrhythmic cardiac-active substance particularly well.

"P-fluorotriamterene" in a concentration of up to 3 $\mu$mol/liter on the left atrium, and up to 100 $\mu$mol/liter on the papillary muscle produces a rise in the threshold of arrhythmia. In concentrations of $>10$ $\mu$mol/liter the threshold of asystole in the papillary muscle is increased, while in concentrations above 1 $\mu$mol/liter the threshold of asystole in the atrium is decreased. Further, a suitable technique for evaluating the anti-arrhythmic and anti-asystolic activity comprises measurement of the action potential on isolated left atria and papillary muscles, using a stimulation frequency of 1 Hz. (See V. Borchard, K. Greeff, and D. Hafner, 1981, *Arzneim.-Forsch./Drug Res.* 31 (II) 10: 1688–1693.)

According to a study by the inventors, the antiarrhythmic activity of "p-fluorotriamterene" is more correctly attributed to an increase of the excitation threshold and an increase in the effective refractory time (prolongation of the action potential), than to a decrease in the $Na^+$ conductivity of the cell membrane, as (the latter effect) is more typical of the large group of the "$Na^+$-inhibitor-type" class 1 anti-arrhythmics (according to Vaughan Williams).

According to normal criteria, the lipophilic character of "p-fluorotriamterene" is greater than that of triamterene. "p-Fluorotriamterene" has only 1/5 the solubility of triamterene in freshly de-mineralized (not distilled) water. It can be made to dissolve to about 0.15% in 75% polyethylene glycol ("PEG 400").

To prepare a lactic acid solution, 25 mg "p-fluorotriamterene" was triturated with 100 mg lactic acid (90% purity, "Merck No. 366"), and water added to make up 25 ml. After heating to 335° Kelvin, a clear solution (pH 2.9) was obtained. When allowed to stand it at 293° K. for a few hours, crystals precipitated. After separation of the solid phase by centrifugation, the "p-fluorotriamterene" content of the solution was determined to be 330 mg/liter.

The distribution coefficient in the system octanol/-phosphate buffer ("Merck Titrisol No. 9879") at pH 7.2 and 294° K. was determined to be 11.0. (For comparison, triamterene in the system octanol/TRIS-buffer at pH 7.4 has distribution coefficient 12.9.)

The compounds having formula I can be administered parenterally or orally. Doses may be in the range of 1 to 100 mg/kg (1 to 100 mg per unit dose).

Pharmaceutical preparations may contain one or more compounds of formula I. These pharmaceutical preparations may be prepared in any customary fashion well known in the art. These preparations may include various excipients and adjuvants. In one embodiment of this invention a pharmaceutical preparation in the form of a solid composition suitable for oral administration, e.g. tablets, capsules, dragees, or the like is presented. Excipients for oral use may comprise pharmaceutically innocuous solids such as mannitol, lactose, organic or inorganic calcium salts, etc. Suitable binders which may be used in accordance with this invention include polyvinyl pyrrolidone, gelatins, or cellulose derivatives. Additional additives may include: tablet-disintegrating agents, e.g. starch or alginic acid; lubricants, e.g. stearic acid or its salts; inorganic flow-promoting agents, e.g. talc or colloidal silicic acid; and flavor modifiers.

The compounds may be mixed with adjuvants and excipients in customary fashion and may be granulated in either the wet or dry state. Depending on the particular added materials employed, it may be possible to produce a directly tablettable powder by simple mixing. The granulate or powder can be loaded directly into capsules, or it can be dressed into tablet cores in any customary fashion.

The therapeutic media for parenteral administration may also be prepared and administered in any customary fashion.

The following example serve to illustrate the manufacture of pharmaceutical compositions comprising at least one compound of formula I. This example is given to illustrate the invention and is not intended to be limiting thereof.

Tablets may be produced by a technique which comprises pressing a mixture of the following composition into tablet cores:

| Material having the composition of formula I | 16.67 kg |
|---|---|
| Lactose | 54.32 kg |
| Cellulose powder | 15.00 kg |
| Talc | 5.08 kg |
| Cornstarch | 2.91 kg |
| Calcium carbonate | 2.50 kg |
| Calcium carboxymethylcellulose | 1.81 kg |
| Magnesium stearate | 0.74 kg |
| Polyvinyl pyrrolidone (m.w. 25,000) | 0.52 kg |
| Highly disperse silicon dioxide | 0.45 kg. |

Obviously, numerous modifications and variations of the present invention are possible in light of the above readings. It is therfore to be understood that within the scope of the appended claims, the invention may be practiced otherwise than as specifically described herein.

What is claimed as new and desired to be secured by Letters Patent of the U.S. is:

1. A pharmaceutical composition comprising an anti-arryhythmic effective amount of a compound of the formula:

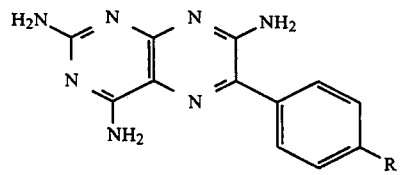

wherein R is a radical selected from the group consisting of, sec-butyl, tert-butyl, neopentyl, cyclohexyl, and benzyl, said composition having anti-arrhythmic cardiac activity.

2. The pharmaceutical composition of claim 1, wherein the active ingredient is present in an amount of from 1 to 100 mg per dose unit.

3. The pharmaceutical composition of claim 1, said composition further comprising mannitol, lactrose, an organic calcium salt or an inorganic calcium salt.

4. The pharmaceutical composition of claim 1, said composition further comprising polyvinyl pyrrolidone, a gelatin or a cellulose derivative.

5. A method for the treatment of cardiac arrhythmias, which comprises administering an anti-arrhythmic effective amount of a compound of the formula:

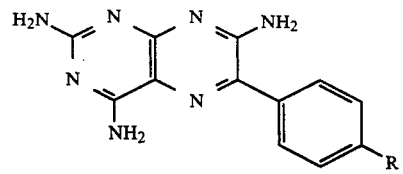

wherein R is a $C_3$ to $C_6$ alkyl group which is saturated or unsaturated, a benzyl group, a trifluoromethyl group, or a nitro group.

6. A method for the treatment of cardiac arrhythmias, which comprises administering an anti-arrhythmic effective amount of compound of the formula:

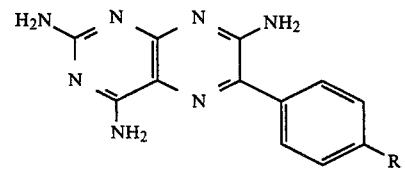

wherein R is a fluorine atom, a chlorine atom, a $C_3$ to $C_6$ alkyl group which is branched or cyclic, a benzyl group, a trifluoromethyl group, or a nitro group.

* * * * *